United States Patent [19]
Denk et al.

[11] Patent Number: 5,034,613
[45] Date of Patent: Jul. 23, 1991

[54] TWO-PHOTON LASER MICROSCOPY

[75] Inventors: Winfried Denk, Zurich, Switzerland; James P. Strickler; Watt W. Webb, both of Ithaca, N.Y.

[73] Assignee: Cornell Research Foundation, Inc., Ithaca, N.Y.

[21] Appl. No.: 436,045

[22] Filed: Nov. 14, 1989

[51] Int. Cl.$^5$ ............................ G01N 21/39; G01J 3/00
[52] U.S. Cl. ............................... 250/458.1; 250/459.1; 250/461.1; 250/462.1; 356/318
[58] Field of Search ............... 250/458.1, 461.1, 462.1, 250/423 P, 459.1; 356/318; 365/127, 106

[56] References Cited

U.S. PATENT DOCUMENTS

| | | | |
|---|---|---|---|
| 4,405,237 | 9/1983 | Illanuccia et al. | 365/301 |
| 4,407,008 | 9/1983 | Schmidt et al. | 358/93 |
| 4,466,080 | 8/1984 | Swainson et al. | 365/106 |
| 4,471,470 | 9/1984 | Swainson et al. | 365/127 |
| 4,631,581 | 12/1986 | Carlsson | 358/93 |
| 4,734,578 | 3/1988 | Horikawa | 250/234 |
| 4,786,170 | 11/1988 | Groebler | 356/318 |
| 4,791,310 | 12/1988 | Honig et al. | 250/458.1 |
| 4,792,341 | 11/1988 | Kozikowski et al. | 8/103 |
| 4,827,125 | 5/1989 | Goldstein | 250/234 |
| 4,838,679 | 6/1989 | Bille | 351/205 |
| 4,863,226 | 9/1989 | Houpt et al. | 350/6.5 |
| 4,877,965 | 10/1989 | Dandliker et al. | 250/458.1 |
| 4,887,721 | 12/1989 | Martin et al. | 209/579 |

OTHER PUBLICATIONS

Ohsawa et al., "On the Possibility of Gas Temperature Measurement Using Two Photon Excitation", Dept. of Applied Physics, Tokyo Univ. of Agriculture & Technology, 21–27 May 1979, pp. 523–528.
Fritzler et al., "A Spectrometer for Semiautomatic Two Photon Fluorescence Spectroscopy", Journal of Physics E: Scientific Inst., 1975, vol. 8, pp. 530–532.
Slomba et al., "A Laser Flying Spot Scanner for Use in Automated Fluorescence Antibody Instrumentation", Journal of the Assoc. for the Advancement of Med. Instrumentation, vol. 6, No. 3, 1972, pp. 230–234.
"Three Dimensional Optical Storage Memory", Parthenopoulos Science, vol. 245, pp. 843–845, Aug. 25, 1989.
"Theory and Practice of Scanning Optical Microscopy", T. Wilson and C. Shepard, Academic Press, London, 1984, pp. 8 and 9.

Primary Examiner—Constantine Hannaher
Assistant Examiner—Edward J. Glick
Attorney, Agent, or Firm—Jones, Tullar & Cooper

[57] ABSTRACT

A laser scanning microscope produces molecular excitation in a target material by simultaneous absorption of two photons to thereby provide intrinsic three-dimensional resolution. Fluorophores having single photon absorption in the short (ultraviolet or visible) wavelength range are excited by a stream of strongly focused subpicosecond pulses of laser light of relatively long (red or infrared) wavelength range. The fluorophores absorb at about one half the laser wavelength to produce fluorescent images of living cells and other microscopic objects. The fluorescent emission from the fluorophores increases quadratically with the excitation intensity so that by strongly focusing the laser light, fluorescence as well as photobleaching are confined to the vicinity of the focal plane. This feature provides depth of field resolution comparable to that produced by confocal laser scanning microscopes, and in addition reduces photobleaching. Scanning of the laser beam, by a laser scanning microscope, allows construction of images by collecting two-photon excited fluorescence from each point in the scanned object while still satisfying the requirement for very high excitation intensity obtained by focusing the laser beam and by pulse time compressing the beam. The focused pulses also provide three-dimensional spatially resolved photochemistry which is particularly useful in photolytic release of caged effector molecules.

21 Claims, 7 Drawing Sheets

TWO-PHOTON LASER MICROSCOPY

This invention was made with Government support under Grant Nos. P41RR04224 awarded by the National Institute of Health; NSF-BBS-8714069 awarded by the National Science Foundation, and NSF-DMB-8609084 awarded by the National Science Foundation. The Government has certain rights in the invention.

BACKGROUND OF THE INVENTION

Although the principle of a flying spot scanner has been known for many years, its application in microscopy has prospered only in the last few years as the necessary technology has been developed. Stable laser light sources and fast electronic image acquisition and storage technology are necessary ingredients for a scanning microscope. While the imaging properties of a non-confocal scanning microscope are very similar to those of conventional microscopes, a new domain is opened by confocal scanning microscopes. The resolution provided by such devices is only moderately increased, but the vastly improved depth discrimination they provide allows the generation of three dimensional images without complicated deconvolution algorithms. The depth discrimination reduces background, and this, together with the use of a single high quality detector such as a photomultiplier, allows quantitative studies with high spatial resolution.

The resolution along the optical axis of a confocal scanning microscope provides useful discrimination against background scattering or fluorescence arising above and below the plane of focus in a transparent object. It is also very helpful in constructing three dimensional fluorescent images from a series of sections and for the use of quantitative fluorescence indicators or for mapping of fluorescent markers of cell surface receptors on non-planar surfaces. Such devices provide slightly better lateral resolution, much better depth field discrimination, and orders of magnitude better background discrimination under ideal conditions than was available with prior devices, under ideal conditions.

Scanning can be carried out either by moving the specimen stage under a stationary beam or by precisely synchronized optical scanning of both the illumination and the fluorescent response signals. Although the moving stage solution is preferable from an optical point of view, it puts limits on sample access and mounting, the use of environmental chambers, and electrical recording with microelectrodes. Accordingly, the moving spot approach is often favored. Such a moving spot may be produced by the use of mirrors mounted on galvonometer scanners, although this limits the obtainable frame frequency. The use of accousto-optical deflectors interferes with the confocal spatial filtering in fluorescence microscopy because of their strong dispersion. Although polygonal mirrors are faster than galvonometer scanners, one alone does not allow a vector mode of operation.

A conventional arc light source can be used for many applications of a confocal scanning microscope which utilizes a rotating disc illuminator, but apparently inescapable intensity modulations limit its use for quantitative applications. In such devices, the image is formed either through a dual set of confocal pin holes in the disc, or, in recent versions, through the illumination pinholes themselves.

Confocal scanning microscopes in which a single point illuminated by a laser is scanned across the moving object work quite well at slow scanning speeds, and good laser scanning micrographs have been obtained using fluorescence markers that absorb and emit visible light. However, confocal scanning images with fluorophores and fluorescent chemical indicators that are excited by the ultraviolet part of the spectrum have not been available, largely because of the lack of suitable microscope lenses, which must be chromatically corrected and transparent for both absorption and emission wavelengths, but also because of the damage done to living cells by ultraviolet light. Furthermore, the limitations of ultraviolet lasers have inhibited such usage.

Fluorescence microscopy is further limited, in all of its manifestations, by the photobleaching of fluorophores in the target material, for the exciting light slowly photobleaches the fluorophores while it is exciting fluorescence. Even in laser scanning confocal fluorescence microscopy, essentially the same photobleaching is incurred as happens in wide field microscopy, because the focused exciting light still illuminates the full depth of the target specimen uniformly, in a time average, as it scans the plane of focus. Photobleaching is particularly troublesome in a three-dimensional image reconstruction because many two-dimensional images are required for this purpose, and the acquisition of each two-dimensional image produces photobleaching throughout the specimen.

SUMMARY OF THE INVENTION

The foregoing difficulties are overcome, in accordance with the present invention, by the use of two-photon molecular excitation of fluorescence in laser scanning microscopy. Two-photon excitation is made possible, in accordance with the present invention, by the combination of (a) the very high, local, instantaneous intensity provided by the tight focusing available in a laser scanning microscope, wherein the laser can be focused to diffraction-limited waist of less than 1 micron in diameter, and (b) the temporal concentration of a pulsed laser. A high intensity, long wavelength, monochromatic light source which is focusable to the diffraction limit such as a colliding-pulse, mode-locked dye laser, produces a stream of pulses, with each pulse having a duration of about 100 femtoseconds ($100 \times 10^{-15}$ seconds) at a repetition rate of about 80 MHz. These subpicosecond pulses are supplied to the microscope, for example by way of a dichroic mirror, and are directed through the microscope optics to a specimen, or target material, located at the object plane of the microscope. Because of the high instantaneous power provided by the very short duration intense pulses focused to the diffraction limit, there is an appreciable probability that a fluorophore (a fluorescent dye), contained in the target material, and normally excitable by a single high energy photon having a short wavelength, typically ultraviolet, will absorb two long wavelength photons from the laser source simultaneously. This absorption combines the energy of the two photons in the fluorophore molecule, thereby raising the fluorophore to its excited state. When the fluorophore returns to its normal state, it emits light, and this light then passes back through the microscope optics to a suitable detector.

The two-photon excitation of fluorophores by highly intense, short pulses of light constitutes a general fluorescence technique for microscopy which provides improved background discrimination, reduces photobleaching of the fluorophores, and minimizes the photo damage to living cell specimens. This is because the focused illumination produced in the microscope fills a converging cone as it passes into the specimen. All of the light which reaches the plane of focus at the apex of the converging cone, except the tiny fraction which is absorbed in the fluorophore, then passes out the opposite side of the specimen through a diverging cone. Only in the region of the focal point on the object plane at the waist formed by the converging and diverging cones is the intensity sufficiently high to produce two photon absorption in the specimen fluorophore, and this intensity dependence enables long wavelength light to provide the effect of short wavelength excitation only in the small local volume of the specimen surrounding the focal point. This absorption is produced by means of a stream of fast, high intensity, femtosecond pulses of relatively long wavelength which retains a moderate average illumination intensity of long wavelength light throughout the remainder of the specimen outside the region of the focal point. As a result, photobleaching of the fluorophore outside the plane of focus is virtually eliminated. One-photon absorption of the long wavelength light is negligible, and outside the plane of focus the instantaneous intensity is too low for appreciable two-photon absorption and excitation, even though the time average illumination is in reality nearly uniform throughout the depth of the specimen. This effect also significantly reduces the damage to living cells.

The two-photon excitation of the present invention allows accurate spatial discrimination and permits quantification of fluorescence from small volumes whose locations are defined in three dimensions, and thus provides a depth of field resolution comparable to that produced in confocal laser scanning microscopes without the disadvantages of confocal microscopes previously described. This is especially important in cases where thicker layers of cells are to be studied. Furthermore, the two-photon excitation greatly reduces the background fluorescence.

The two-photon absorption technique discussed above can also be used to excite selected locations in a three-dimensional optical memory device of the type described by Dimitri A. Parthenopoulos et al in an article entitled "Three-dimensional Optical Storage Memory", Science, Vol. 245, pages 843–845, Aug. 25, 1989. In that device, selected locations in a matrix are illuminated by two beams of different wavelengths which overlap in time and space to produce absorption. In accordance with the present invention, extremely short, high intensity pulses of relatively long wavelength light from a single laser source, or from coaxial multiple sources, are directed through a scanning microscope into a storage medium which may be a photochromic or a photolyzable fluorescent material such as crystals, composites, or chomophores embedded in a polymer matrix. The incident light beam is highly focused onto any one of many layers in the matrix, and its intensity is modulated as it is scanned or stepped across the selected layer. The beam excites selected locations in the matrix so that coded information represented by the beam is stored in a binary format within the medium. The highly focused beam provides the spatial resolution required for accurate storage. The femtosecond, high intensity pulses induce two-photon absorption in the matrix material to write information into the material, which normally requires excitation by light in the ultraviolet range. The excitation level of the written points in the matrix can be detected, or read, by a "read" laser of long wavelength which will produce fluorescence in the previously written molecules.

BRIEF DESCRIPTION OF THE DRAWINGS

The foregoing, and additional objects, features and advantages of the present invention will become apparent from the following detailed description of preferred embodiments thereof, taken in conjunction with the accompanying drawings, in which.

DESCRIPTION OF PREFERRED EMBODIMENT

Figure 1:
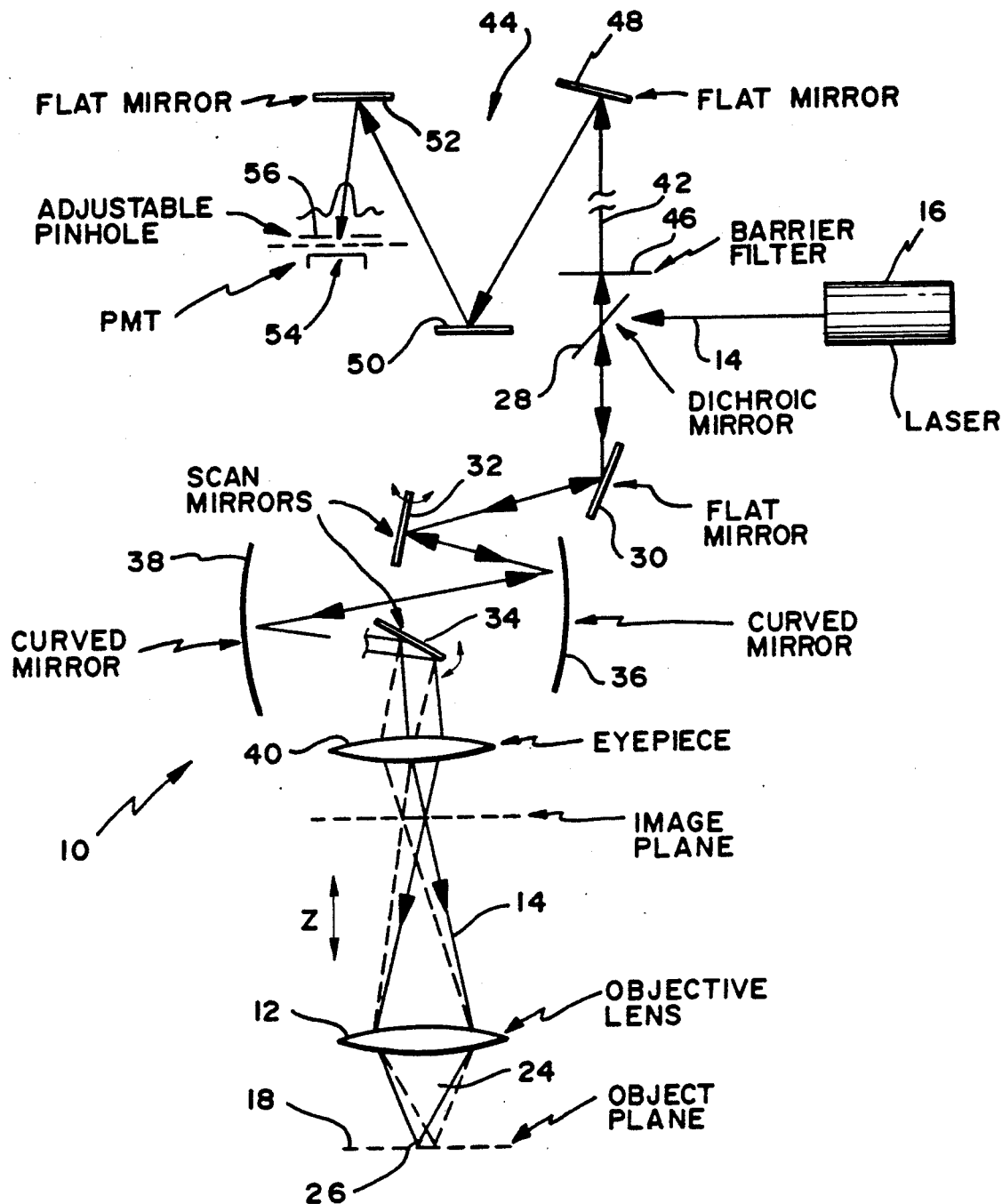
FIG. 1 is a diagrammatic illustration of a laser scanning confocal microscope utilized in accordance with the present invention.
Figure 1A:
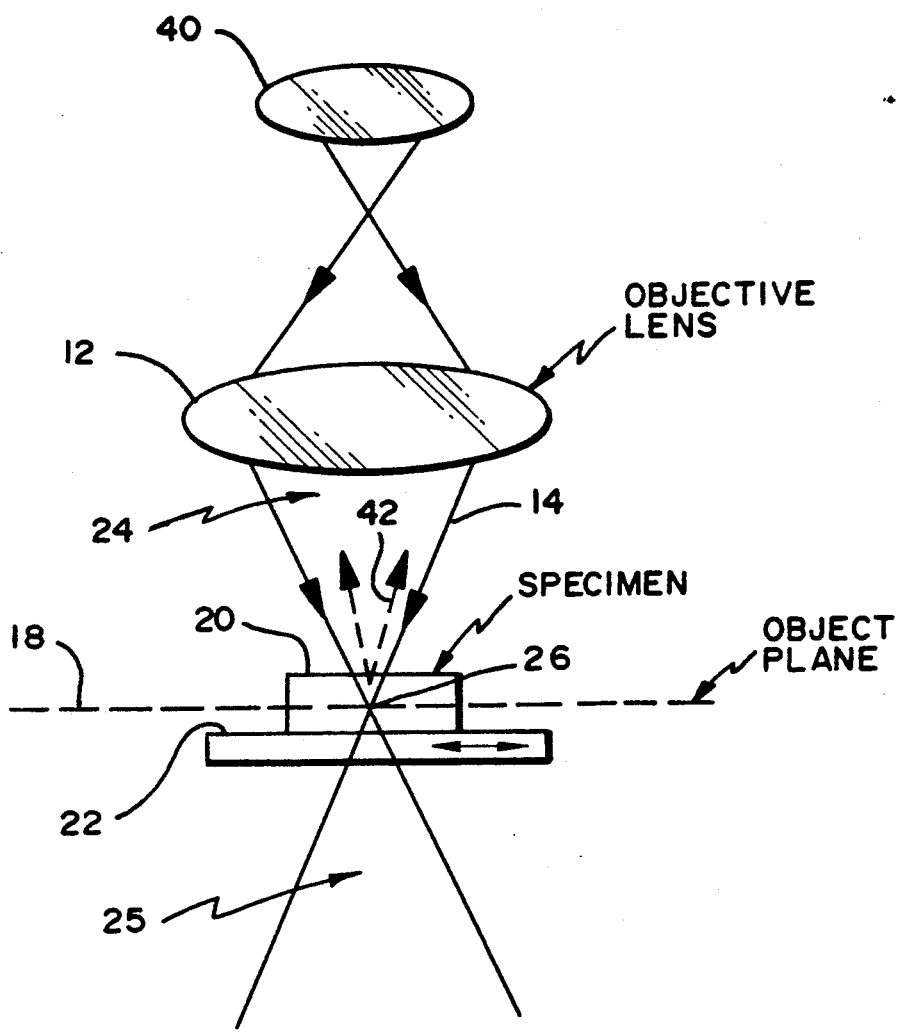
FIG. 1A is an enlarged partial view of the region of the object plane of the device of FIG. 1.

Turning now to a more detailed description of the present invention, there is illustrated in FIG. 1 in diagrammatic form a conventional laser scanning microscope 10 which includes an objective lens 12 for focusing incident light 14 from a source 16 such as a laser onto an object plane 18. As illustrated in FIG. 1A, the object plane may lie on, or in, a specimen or target material 20 which may be carried on a movable stage 22. The illumination provided by incident light beam 14 fills a converging cone generally indicated at 24, the cone passing into the specimen 20 to reach the plane of focus at object plane 18 and, except for the tiny fraction of light absorbed by the specimen, passing out through a diverging cone 25. The incident light forms a waist, or focal point, 26 on the object plane 18. The diameter of the focal point 26 is limited by diffraction in the optical path, but preferably is less than 1 micron. As is known, by adjustment of the microscope optics, the vertical location of the focal point in the specimen 20 can be selected. Additionally, the stage 22 may be movable in a horizontal plane, as in a raster motion along X and Y axes, to position the incident light at selected locations in the specimen in the horizontal plane, so that three-dimensional scanning of the specimen can be obtained. However, since mechanically scanned stages present difficulties, it is preferred to use a stationary stage, and to scan the incident beam in the X-Y plane optically, as by means of scanning mirrors in the optical path of the microscope.

The optical path from laser 16 to the object plane 18 includes a dichroic mirror 28 onto which the light from the laser 16 is directed. As will be explained in greater detail below, in accordance with the present invention the output from the laser consists of short intense pulses of light having a relatively long wavelength, preferably in the visible red or near infrared spectral range. The mirror 28 deflects this long wavelength light downwardly to a mirror 30 which in turn directs the light to a pair of scanning mirrors 32 and 34 by way of curved mirrors 36 and 38. The mirrors 32 and 34 are rotatable about mutually perpendicular axes in order to move the incident light 14 along perpendicular X and Y axes on the object plane so that the stationary specimen is scanned by the incident beam. The light from the scanning mirrors passes through eyepiece 40 and is focused through the objective lens 12 to the object plane 18.

Fluorescence produced in the specimen 20, indicated by dotted arrows 42 in FIG. IA, travels back through the microscope 10, retracing the optical path of the incident beam 14, and thus passes through objective lens 12 and eyepiece 40, the scanning mirrors 34 and 32 and the curved mirrors 38 and 36, and is reflected by mirror 30 back to the dichroic mirror 28. The light emitted by fluorescent material in the specimen is at a wavelength that is specific to the fluorophore contained in the specimen, and thus is a different wavelength than the incident light 14. This fluorescent light is able to pass through the dichroic mirror 28, rather than being reflected back toward the laser 16, and follows the light path indicated generally at 44. The fluorescent light 42 thus passes through a barrier filter 46 and is reflected by flat mirrors 48, 50 and 52 to a suitable detector such as a photomultiplier tube 54. In accordance with the present invention, a confocal laser scanning microscope is preferred, and accordingly such a microscope is illustrated in the drawings. However, it will be understood that other laser scanning microscopes may be used. In the confocal microscope 10, an adjustable confocal pin hole 56 is provided in the collection optics 44 to minimize background fluorescence excited in the converging and diverging cones 24 and 25 above and below the plane of focus. This confocal pinhole is useful, but is not necessary in the two photon fluorescence excitation of the present invention, since excitation is essentially limited to the region of the focal point 26 on the object plane.

With prior fluorescence microscopes the visible light fluorescence photons 42 are produced by molecules that are excited by absorbing a single photon from incident light 14 that has higher energy; that is, a shorter wavelength, than the fluorescence 42 generated during relaxation of the molecule from its excited state. The number of fluorescence photons released per molecule in such prior devices is ordinarily linearly proportional to the number of exciting photons absorbed. Because only a single photon need be absorbed in such devices, photolysis of molecules that absorb the exciting light 14 can occur all along the double cone beam 24 and 25 within the specimen 20, although this process is not necessarily linear with intensity. Because fluorescence is generated all along the double cone beam, the amount of fluorescence released from each plane in the specimen above, below and within the plane of focus of the exciting light 14 tends to be the same, and three dimensional resolution is difficult to obtain. As a result, the high energy of the incident light throughout the specimen tends to damage the specimens and this is particularly undesirable when living cells are being viewed.

In order to obtain three dimensional resolution in scanning microscopy and to reduce damage to the specimen in regions outside the focal point of the microscope, the present invention utilizes two-photon excitation of a fluorophore which has a one-photon absorption peak at a wavelength which overlaps one-half that of the exciting light. To accomplish this, the laser 16 produces a very short pulsed laser beam of high instantaneous power and of a relatively long wavelength, for example in the visible red or the infrared range. This light is directed to a specimen containing a fluorophore normally excited by a single photon in the short wavelength, for example ultraviolet, range so that two low energy (red) photons must combine their energy to provide the same excitation of the specimen that would be provided by a single high energy (ultraviolet) photon. Both the excitation and hence the fluorescence rates in the specimen are proportional to the square of the intensity of the incident light. In the focused excitation laser beam 14, the intensity of the long wavelength incident light becomes high enough to excite the fluorophores in the specimen only in the region of the focal point 26 of the microscope optics. This focal point may be adjustably positioned within the specimen, so that fluorescence and/or photolysis of the specimen are produced only in a selected ellipsoidal volume around the focus. Thus, in accordance with the invention, only long wavelength excitation light has to pass through the specimen, and this long wavelength light is focused to produce sufficient intensity to excite fluorescence only in a very small region. This fluorescence is produced even if the fluorophore normally absorbs only in the ultraviolet. Since the focal point can be selectively positioned in the specimen, three-dimensional resolution is provided in both scanning fluorescence microscopy and in photolysis, including photolysis of photon-activatable reagents which ca be released by photolysis.

In accordance with the present invention, the necessary excitation intensity is provided at the focal point of the microscope 10 from a light source 16 which may be, for example, a colliding pulse, mode-locked dye laser generating pulses of light having a wavelength in the red region of the spectrum, for example about 630 nm, with the pulses having less than 100 fsec. duration at about 80 MHz repetition rate. Other bright pulsed lasers may also be used to produce light at different relatively long wavelengths in the infrared or visible red region of the spectrum, for example, to generate the necessary excitation photon energies which will add up to the appropriate absorption energy band required by the fluorophores in the specimen which normally would be excited by absorption of a single photon in the spectral region having wavelengths about one-half the wavelength of the incident light. Thus, for example, two photons in the visible red region at 630 nm would combine to excite a fluorophore which normally absorbs light in the ultraviolet region at 315 nm, while two photons in the infrared region of, for example, 1070 nm, would excite a fluorophore which absorbs at 535 nm in the visible light region.

In a modified form of the invention, the single wavelength light source 16 can be replaced by two different long wavelength laser sources so that the incident light beam 14 consists of two superimposed pulsed light beams of high instantaneous power and of different wavelengths. The wavelengths of the incident beam are selected to excite a fluorophore which is absorbent at a short wavelength which may be described as:

$$1/\lambda_{abs} = 1/\lambda_1 + 1/\lambda_2$$

where $\lambda_{abs}$ is the short wavelength of the absorber, and $\lambda_1$, $\lambda_2$ are the laser incident beam wavelengths..

In two-photon excitation, with a typical two-photon cross section $\delta$ of:

$$\delta = 10^{-58} m^4 s/photon \qquad (eq.\ 1)$$

with the pulse parameters given above (100 fsec. pulses at a repetition rate of 80 MHz), and with the beam focused by a lens of numerical aperture A=1.4, the average incident laser power ($P_0$) of approximately 50 mW saturates the fluorescence output of a fluorophore at the limit of one absorbed photon per pulse per fluorophore. The number $n_a$ of photons absorbed per fluorophore per pulse depends on the following relationship:

$$n_a \approx \frac{P_0^2 \delta}{\tau f^2} \left[ \frac{A^2}{2hc\lambda} \right]^2 \qquad (Eq.\ 2)$$

where
- $\tau$ is the pulse duration;
- f is the repetition rate;
- $P_0$ is the average incident laser power;
- $\delta$ is the photon absorption cross section;
- h is the Planck quantum of action;
- c is the speed of light; and
- A is the numerical aperture of the focusing lens.

The fluorescence emission could be increased, however, by increasing the pulse repetition frequency up to the inverse fluorescence lifetime, which typically is:

$$\tau_f^{-1} = 10^9 s^{-1} \qquad (Eq.\ 3)$$

For comparison, one-photon fluorescence saturation occurs at incident powers of about 3 mW.

Figure 2:
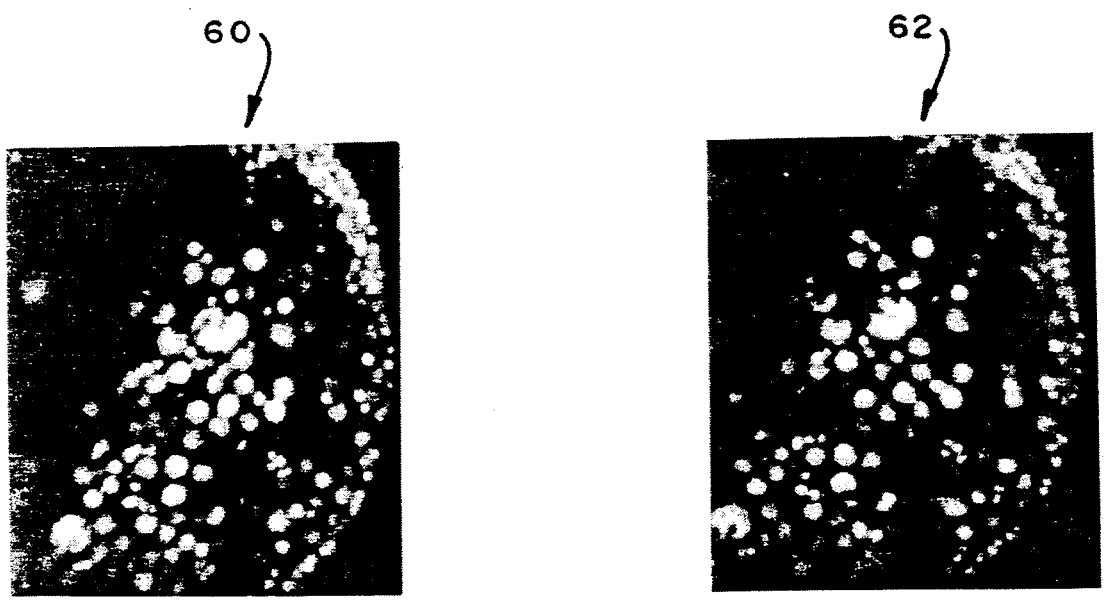
FIG. 2 is a synthesized stereo image pair showing blue fluorescence excited by two-photon absorption of red light.

FIG. 2 illustrates the depth discrimination achieved by the two photon technique of the present invention. A stereo pair of images 60 and 62 was generated from a stack of images of a cluster of fluorescent 9 micrometer diameter latex beads which are normally excited by ultraviolet light having a wavelength of about 365 nm. These images were obtained using a standard laser scanning microscope, but with its continuous-wave argon-ion laser illuminator 16 replaced by a 25 mw colliding-pulse mode-locked dyelaser producing output pulses at a wavelength of about 630 nm. Measurements made on the microscope 10 indicated that about 3 mw reached the object plane. An emission filter, passing wavelengths from 380 to 445 nm, was provided at the barrier filter 46, and the detector aperture 54 was opened to its limit in order to reduce the optical sectioning effect that would result from a small confocal aperture.

Figure 3:
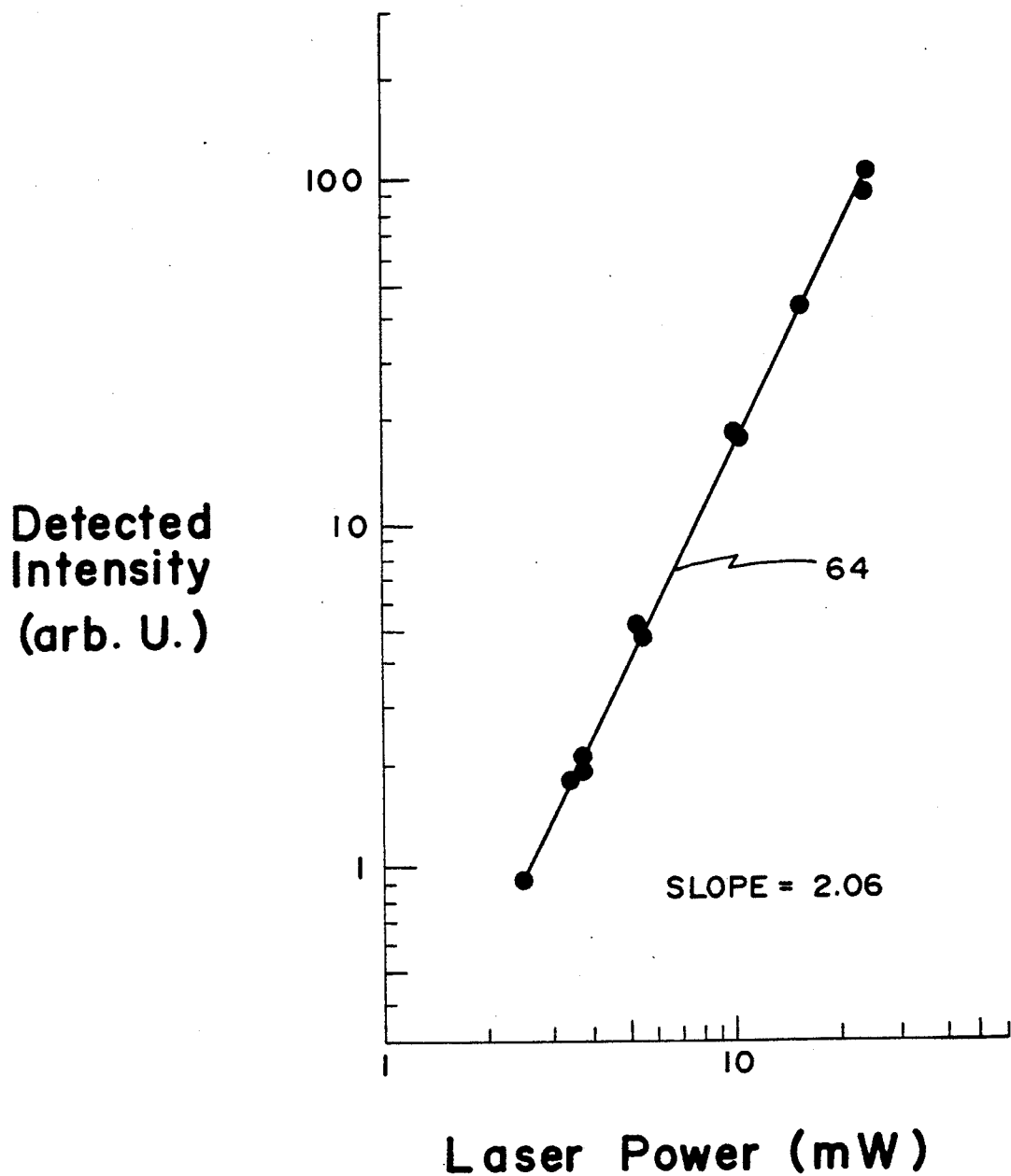
FIG. 3 is a plot of the average intensity from an area inside a fluorescent latex bead versus the applied average laser power.

The intensity of the incident beam 14 from laser 16 was adjusted by placing neutral density filters in the excitation beam between laser 16 and the dichroic mirror 28 and the blue fluorescence produced by the individual latex beads was measured. As illustrated in FIG. 3 by the graph 64, the detected intensity of fluorescence from the latex beads making up the specimen increased with the square of the excitation laser power, clearly indicating two-photon excitation in the beads. The excitation cross section of the beads, which were "fluoresbrite BB" beads produced by Polysciences Corporation, was estimated to be $5 \times 10^{-58}$ m s/photon, accurate within a factor of 3, by taking into account the dye concentration in the beads, the optical throughput of the laser scanning microscope, the pulse duration, the repetition rate, the numerical aperture and the incident power. This value was found to be comparable to previously measured values for similar dyes.

Figure 4:
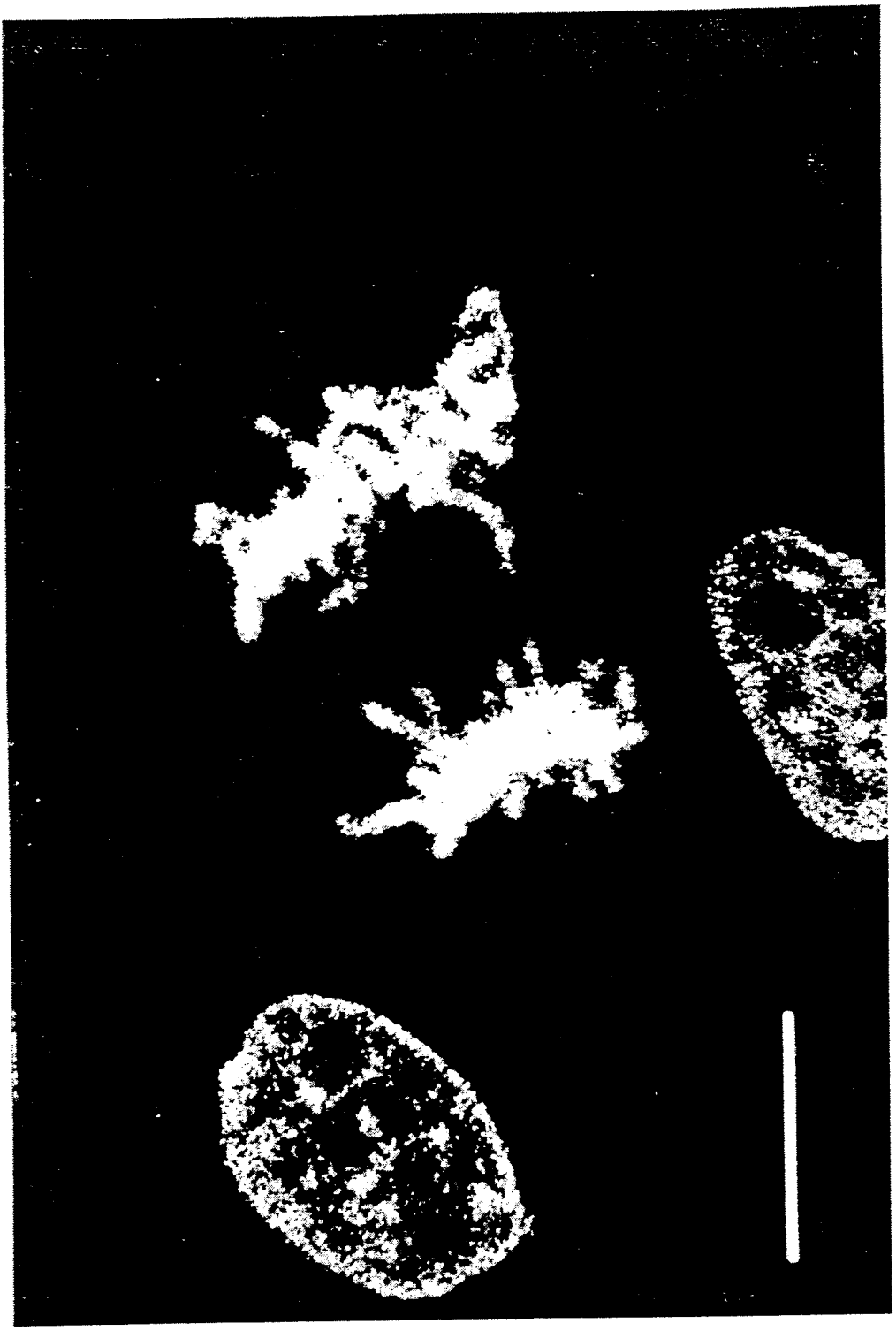
FIG. 4 is a two-photon excited fluorescence image of chromosomes of live cultured pig kidney cells stained with a DNA stain.

FIG. 4 is a scanned image of chromosomes in dividing cells (LLC-PK1; ATTC), using cellular DNA labeling with an ultraviolet excitable fluorescent stain (33258; Hoechst) the image acquisition time of 13 seconds was short compared to the bleaching time of several minutes. Furthermore, no degradation was apparent in these live cells even after illumination by the scanning laser for several minutes.

Figure 5:
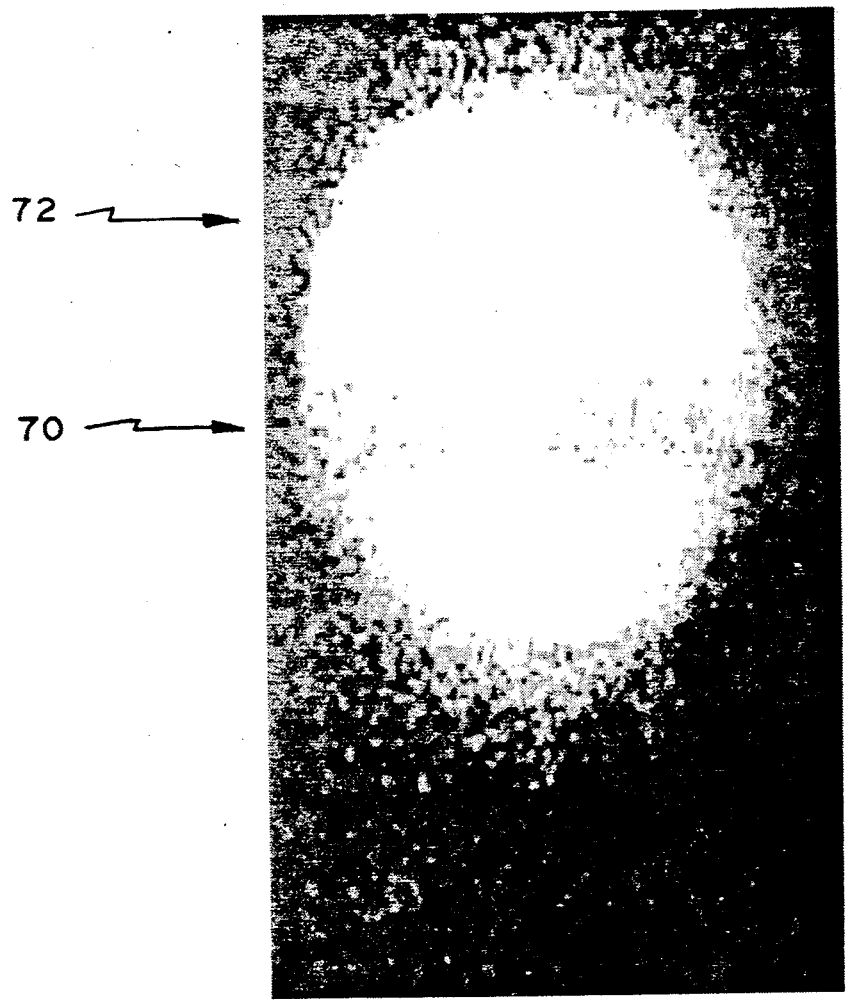
FIG. 5 is an image of a latex bead, showing two-photon photobleaching confined to the plane of focus.
Figure 6:
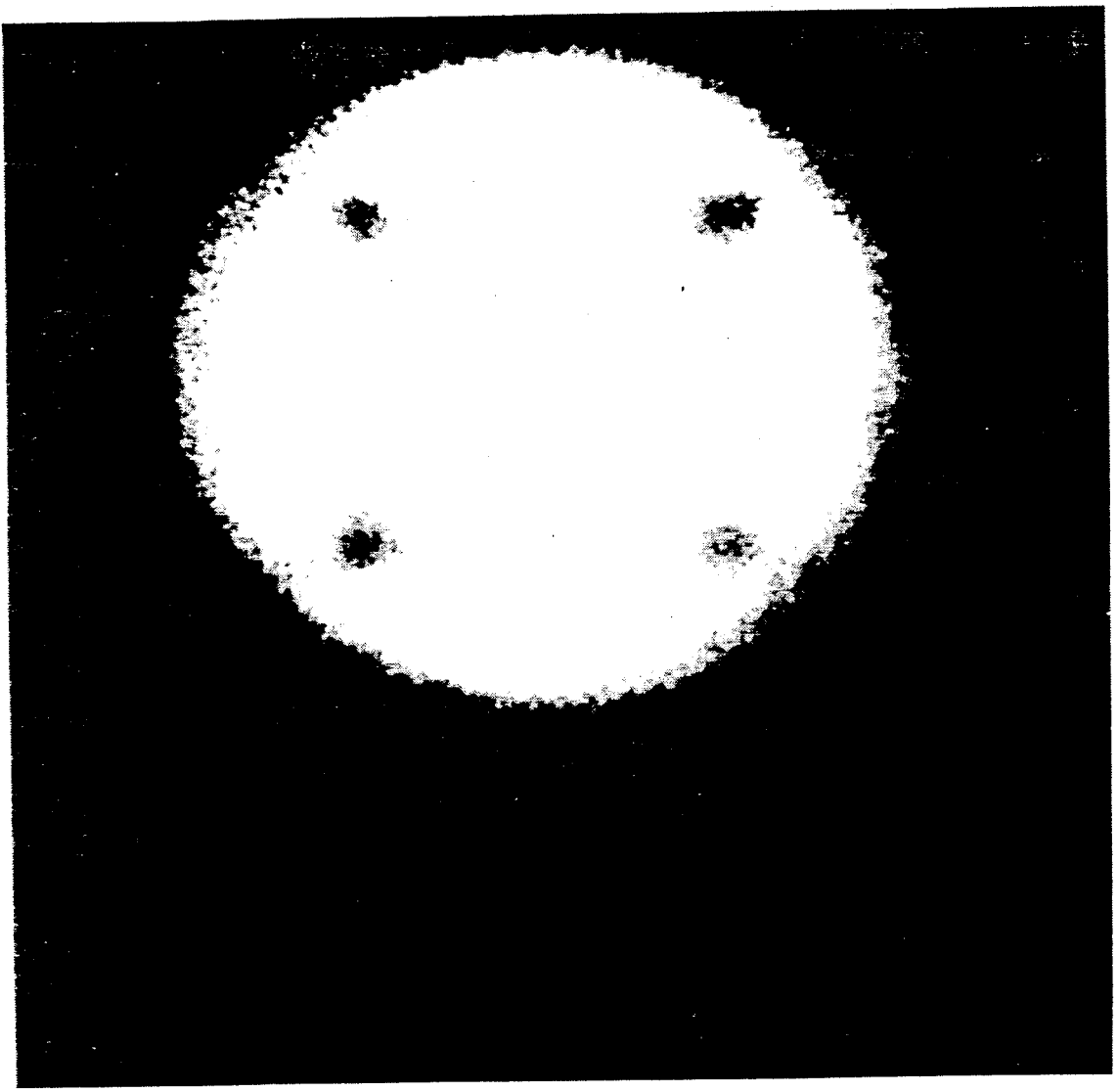
FIG. 6 is an image of a two-photon bleached pattern inside a fluorescently stained latex bead.

Photobleaching during protracted scanning of a fluorescent bead occurred only in a slice about 2 micrometers thick around the focal plane, as demonstrated by the horizontal section 70 of reduced brightness bleached out of the bead 72 illustrated in FIG. 5. This bead was scanned for six minutes at a constant focal plane position. Similar localization of bleaching was observed in the fluorescently stained cell nuclei. This localization illustrates a distinct advantage over the use of single-photon excitation, where the entire specimen is bleached even when only a single plane is imaged. This is because for one-photon excitation, bleaching in both scanning and broad field microscopy depends on the time averaged excitation intensity, which does not vary along the axial, or Z-direction indicated in FIG. I. For two-photon excitation, on the other hand, bleaching depends on the time averaged square of the intensity, which falls off strongly above and below the focal plane.

The dependence of the fluorescent signal on the square of the excitation intensity is responsible for another advantage of two-photon excitation; that is, such excitation provides an optical sectioning effect through the specimen, even when using a detector, such as a CCD array, which views the whole field, without a pinhole being used as a spatial filter. This sectioning effect, which is illustrated in FIG. 5, avoids the serious problems associated with chromatic aberration in the objective lens and some of the throughput losses in conventional confocal laser scanning microscopes.

Two-photon photolysis can also be used for fast and localized release of biologically active chemicals such as caged Ca++, H+, nucleotides and neurotransmitters. For example, when caged neurotransmitters are released by a scanning beam, the whole-cell transmembrane current so produced is usable as the contrast-generating mechanism to map the distribution of receptor activity for those transmitters on the cell surface. The feasibility of two-photon cage photolysis was demonstrated, in accordance with the present invention, by irradiating DMNPE caged ATP (33mM) [from Molecular Probes, Eugene Oregon], by the colliding pulse mode locked dyelaser 16 focused to a beam waist diameter at the object plane of about 10 micrometers. Photolysis yields of about $10^{-11}$ moles of ATP were measured using a luciferin bioluminescence assay from Calbiochem, San Diego, CA. Typically, about 10% of the caged ATP in an aliquot volume of about $10^7 (\mu m)^3$ was photolyzed in the illumination volume of about $10^4 (\mu m)^3$ during about 600 seconds.

Since two-photon excitation in accordance with the present invention provides access by visible light to excitation energies corresponding to single-ultraviolet-photon excitation, a whole new class of fluorophores and fluorescent indicators becomes accessible to three-dimensionally resolved laser scanning microscopy. Such indicators may be Indo-1 for $Ca^+$, Mag-Indo-1 for $Mg^{+2}$, ABF1 for $Na^+$ and PBFI for $K^+$. Although two-photon cross sections are not yet known for many of these compounds, and different selection rules apply to two-photon absorption, molecular asymmetry often allows both one photon and two-photon transitions into the same excited state. Visible fluorescence was observed from 10mM solutions of Indo-1, FURA-2, Hoechst 33258, Hoechst 33342, DANSYL hydrazine [Molecular Probes], Stilbene 420 [Exciton Chem. Co., Dayton, OH], and several Coumarin dyes upon excitation by a CMP weakly focused to a 25 µm diameter waist, and two-photon excited LSM fluorescence images of microcrystals of DANSYL and Coumarin 440 were recorded.

Another application of the present invention may be in three-dimensional optical memory devices which rely on multi-photon processes in two intersecting beams for writing and reading operations. A single beam would be simpler than the two intersecting beams, and would permit maximal information packing density. The multi-photon processes would be localized to the high intensity region at the focus, as illustrated in FIG. 5 where the bleaching of microscopic patterns inside fluorescent beads constitutes a high density write once memory which is readable about $10^3$ times with present fluorophores.

Thus there has been described and illustrated a practical two-photon laser scanning fluorescence microscope for biological and other applications. The two-photon excited fluorescence microscope provides inherent three-dimensional resolution with a depth of field comparable to that produced by confocal laser scanning microscopes. The use of a confocal pinhole in conjunction with this two-photon excitation further improves resolution along all three axes. Background fluorescence can be eliminated by scaled subtraction of images which are recorded at different input powers. With the present technique, photobleaching, as well as photodynamic damage, can be confined to the vicinity of the focal plane, thereby providing a considerable advantage over both confocal laser scanning microscopy and area detector imaging for the acquisition of data for three dimensional reconstruction, since ultraviolet damage to cells and fluorophores would be confined to the volume from which information is actually collected. This also allows sharp localization of photochemical processes such as photolysis and photoactivation within the focal volume. The invention is principally described as utilizing two photons from a single laser, but it should be understood that excitation of the target material can also be accomplished by two photons from two sources, as long as the two different wavelengths add up to the excitation wavelength of the target material. Thus, for example, two different laser sources could be used, with their output beam being directed coaxially into the optical path of the microscope. Alternatively, two different wavelengths could be derived from a single source, as by means of a frequency doubler.

Although the present invention has been described in terms of preferred embodiments, it will be apparent to those of skill in the art that variations and modifications may be made without departing from the true spirit and scope thereof as set forth in the accompanying claims.

What is claimed is:

1. A laser scanning microscope comprising:
    stage means for receiving target material to be imaged, the target material including fluorescent means responsive to excitation by photons in a short wavelength spectral range to produce characteristic fluorescence;
    lens means positioned to direct light toward said stage and having an object plane in target material at said stage means;
    a source of subpicosecond monochromatic coherent light pulses of high instantaneous energy intensity comprised of photons in a long wavelength spectral range to which target material at said stage does not respond by single photon excitation to produce its characteristic fluorescence, said pulses having a high repetition rate;
    detector means;
    means directing said coherent light pulses along an optical path including said lens means to impinge on target material at said stage means, said lens means focusing said light pulses at said object plane so that said long wavelength light pulses provide sufficient instantaneous intensity to produce in target material at said object plane simultaneous absorption of two incident photons to thereby excite characteristic fluorescence in target material at said stage means, said fluorescence providing output light which travels on said optical path to detector means.

2. The microscope of claim 1, wherein said light source produces subpicosecond pulses of sufficient instantaneous intensity and repetition rate that target material at said stage means will absorb energy simultaneously from at least two incident long wavelength photons substantially only in said object plane.

3. The microscope of claim 1, wherein said lens means is located with respect to said stage means to focus said long wavelength light from said source to a submicron diameter at said object plane to produce a sufficiently high intensity at said object plane to produce fluorescence in target material at said stage means and insufficient intensity outside said focal plane to produce such fluorescence.

4. The microscope of claim 1, wherein said lens means is arranged to focus said long wavelength light into a conical configuration to produce converging and diverging light on opposite sides of said object plane, whereby said long wavelength light is concentrated at a focal point on said plane.

5. The microscope of claim 1, further including target material carried by said stage means, and wherein said long wavelength light from said source is in the red wavelength spectral range, and wherein said lens means focuses said light at a focal point in said target material at said stage means, said target material being a fluorophore having a single photon absorption peak in the ultraviolet wavelength spectral range and being capable of absorbing two photons in the red wavelength spectral range to produce fluorescence.

6. The microscope of claim 5, wherein said lens means is located to focus said long wavelength light at a focal point in said target material to produce a light intensity which excites fluorescence in a limited ellipsoidal volume around said focal point.

7. A laser scanning microscope, comprising
    stage means for receiving a target material having an absorption energy level peak responsive to single photon excitation by light of a predetermined wavelength;
    lens means positioned to direct light to said stage means and having an object plane in target material at said stage means;

a laser source of subpicosecond a laser light pulses, said laser light having a wavelength about twice said predetermined wavelength;

mirror means directing said laser light pulses along an optical path including said lens means to cause said pulses to impinge on target material at said object plane, said lens means focusing said laser light pulses on a focal point in the target material, the intensity of said pulses producing in the region of said focal point a two-photon excitation energy level equivalent to the single-photon excitation energy level which corresponds to said single photon absorption peak..

8. The microscope of claim 7, wherein said long wavelength light is in the red wavelength spectral range, and wherein said lens means focuses said light at a focal point in target material at said stage means, said target material including a fluorophore having said absorption peak.

9. The microscope of claim 7, wherein said long wavelength impinging light pulses provide photons of light energy in the red wavelength spectral range to target material at said stage, and wherein the combined energy of two photons of said impinging light is required to produce fluorescence therein.

10. The microscope of claim 9, wherein said lens means is adjustable to select focal points at different depths within target material at said stage means.

11. The microscope of claim 10, further including scanning means to move said focal point with respect to target material at said stage means.

12. The microscope of claim 11, further including detector means responsive to light in said optical path for detecting fluorescence produced by target material at said stage means.

13. The microscope of claim 12, wherein said detector means is a photosensitive array which responds to said fluorescence.

14. The microscope of claim 7, further including target material at said object stage, wherein said target material is a biological cell responsive to said two-photon excitation energy level produced at said focal point by said light pulses.

15. The microscope of claim 14, wherein said target material at said stage means includes means responsive to said light pulses at said focal point to produce localized release of biologically active chemicals.

16. The microscope of claim 7, further including target material at said object stage, wherein said target material is a photon-activatable reagent.

17. A method of fluorescence microscopy by a two-photon excitation technique, comprising:

providing a sample containing fluorescent molecules which radiate photons of a first characteristic energy;

illuminating said sample with a beam of rapidly repeating, intense, subpicosecond pulses of laser light comprising photons of a second characteristic energy, wherein said second characteristic energy is about one-half said first characteristic energy;

focusing said illumination to a focal point having a submicron diameter with said sample to produce an illumination intensity sufficiently high at said focal point to produce molecular excitation and fluorescence of said sample by simultaneous absorption of two incident photons;

scanning the submicron diameter focal point of said beam in a raster pattern through said sample; and detecting the fluorescence produced by said sample.

18. The method of claim 17, wherein said step of illuminating includes directing a beam of light having an illumination intensity sufficient to produce molecular excitation substantially only at said focal point to thereby suppress background fluorescence.

19. The method of claim 17, wherein said step of illuminating includes directing a beam of light having an illumination intensity sufficient to produce molecular excitation substantially only at said focal point to thereby suppress photobleaching of said sample material at locations outside the focal plane.

20. The method of claim 17, wherein the step of providing a sample includes providing a sample of a living biological specimen.

21. A method for producing localized photolytic release of caged biologically active compounds by a two-photon excitation technique, comprising:

providing a sample containing caged biologically active molecules which are excitable by photons of a first characteristic energy;

illuminating said sample with a beam of rapidly repeating, intense, subpicosecond pulses of laser light comprising photons of a second characteristic energy wherein said second characteristic energy is about one-half said first characteristic energy;

focusing said illumination to a focal point within said sample to produce an illumination intensity sufficiently high only at said focal point to produce molecular excitation and consequent release of caged biologically active compounds by simultaneous absorption of two incident photons of said second characteristic energy.

* * * * *